United States Patent
Surnilla et al.

(10) Patent No.: US 9,382,880 B2
(45) Date of Patent: Jul. 5, 2016

(54) METHODS AND SYSTEMS FOR A GAS CONSTITUENT SENSOR

(71) Applicant: Ford Global Technologies, LLC, Dearborn, MI (US)

(72) Inventors: Gopichandra Surnilla, West Bloomfield, MI (US); Richard E. Soltis, Saline, MI (US); Jacobus Hendrik Visser, Farmington Hills, MI (US); Timothy Joseph Clark, Livonia, MI (US); David James Scholl, Huntington Woods, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 564 days.

(21) Appl. No.: 13/706,074

(22) Filed: Dec. 5, 2012

(65) Prior Publication Data

US 2014/0150760 A1 Jun. 5, 2014

(51) Int. Cl.
*F02M 25/07* (2006.01)
*G01N 33/00* (2006.01)
*F02B 47/08* (2006.01)
(Continued)

(52) U.S. Cl.
CPC .............. *F02M 26/46* (2016.02); *F02B 47/08* (2013.01); *F02D 41/005* (2013.01); *F02D 41/144* (2013.01); *F02D 41/1456* (2013.01); *F02M 35/1038* (2013.01); *F02M 35/10393* (2013.01); *G01N 33/0006* (2013.01); *F02D 2200/0406* (2013.01); *F02M 25/089* (2013.01); *Y02T 10/47* (2013.01)

(58) Field of Classification Search
CPC .............. F02M 2025/0762; F02M 2025/0763; F02M 25/0753; F02M 25/0755; F02M 35/1038; F02B 47/08; F02D 41/005; F02D 41/1438; F02D 41/1439; F02D 41/144; F02D 41/1441; F02D 41/1456; Y02T 10/47; G01N 33/0006
USPC ............. 123/568.11, 568.12, 568.15, 568.16, 123/568.21, 688, 698, 704, 693, 694; 73/1.02, 1.03, 1.06, 23.2, 23.21, 23.31, 73/23.32; 701/102, 108, 109
See application file for complete search history.

(56) References Cited

U.S. PATENT DOCUMENTS 4,614,175 A * 9/1986 Asayama ............ F02D 41/0052
123/568.26
4,727,849 A * 3/1988 Nishida ............... F02D 41/0052
123/568.27
(Continued)

FOREIGN PATENT DOCUMENTS

GB 2501705 A * 4/2012
GB 2501705 A * 6/2013
(Continued)

*Primary Examiner* — Stephen K Cronin
*Assistant Examiner* — Brian Kirby
(74) *Attorney, Agent, or Firm* — Julia Voutyras; Alleman Hall McCoy Russell & Tuttle LLP

(57) ABSTRACT

Various systems and methods are described for an engine system with an exhaust gas recirculation system. In one example method, a correction for a gas constituent sensor is determined based on output from the gas constituent sensor and output from a pressure sensor over a range of boost pressure. The gas constituent sensor output is adjusted based on the correction, and an amount of exhaust gas recirculation is adjusted based on the adjusted gas constituent sensor output.

17 Claims, 4 Drawing Sheets

(51) Int. Cl.
*F02M 35/10* (2006.01)
*F02D 41/14* (2006.01)
*F02D 41/00* (2006.01)
*F02M 25/08* (2006.01)

(56) References Cited

U.S. PATENT DOCUMENTS

| | | | | |
|---|---|---|---|---|
| 4,790,286 A * | 12/1988 | Nishida | | F02D 41/0052 |
| | | | | 123/568.27 |
| 4,836,174 A * | 6/1989 | Chujo | | F02D 41/144 |
| | | | | 123/676 |
| 4,905,654 A | 3/1990 | Katsuno et al. | | |
| 5,535,614 A * | 7/1996 | Okamoto | | G01N 27/185 |
| | | | | 338/22 R |
| 5,644,068 A * | 7/1997 | Okamoto | | G01N 27/185 |
| | | | | 374/44 |
| 5,908,023 A * | 6/1999 | Stutzenberger | | B01D 53/22 |
| | | | | 123/585 |
| 6,631,632 B2 * | 10/2003 | Matsubara | | F02D 41/144 |
| | | | | 73/1.06 |
| 6,739,177 B2 * | 5/2004 | Sato | | F02D 41/0037 |
| | | | | 73/114.71 |
| 6,742,379 B2 * | 6/2004 | Matsubara | | F02D 41/144 |
| | | | | 73/1.06 |
| 7,013,905 B2 * | 3/2006 | Jones | | G05D 11/138 |
| | | | | 137/12 |
| 7,415,389 B2 * | 8/2008 | Stewart | | G05B 11/42 |
| | | | | 700/26 |
| 7,610,142 B1 * | 10/2009 | Hoard | | F01N 13/008 |
| | | | | 60/274 |
| 7,614,391 B2 * | 11/2009 | Kawase | | F02D 41/123 |
| | | | | 123/674 |
| 7,957,919 B2 * | 6/2011 | Marconi | | F02D 41/123 |
| | | | | 702/45 |
| 8,521,354 B2 * | 8/2013 | Sasaki | | F02D 41/0072 |
| | | | | 701/29.1 |
| 8,601,813 B2 * | 12/2013 | Shutty et al. | | 60/605.2 |
| 8,630,787 B2 * | 1/2014 | Shutty et al. | | 701/108 |
| 8,904,787 B2 * | 12/2014 | Styles | | F02D 9/02 |
| | | | | 60/605.2 |
| 2002/0139360 A1 * | 10/2002 | Sato | | F02D 41/0037 |
| | | | | 123/698 |
| 2007/0169748 A1 * | 7/2007 | Nakayama | | F02D 35/02 |
| | | | | 123/435 |
| 2009/0283075 A1 | 11/2009 | Yamazaki et al. | | |
| 2010/0000213 A1 * | 1/2010 | Onishi | | F02D 41/0007 |
| | | | | 60/602 |
| 2010/0101226 A1 * | 4/2010 | Shutty | | F02D 41/0072 |
| | | | | 60/602 |
| 2010/0139245 A1 * | 6/2010 | Scheuerer | | F02D 41/123 |
| | | | | 60/276 |
| 2010/0186726 A1 * | 7/2010 | Takagi | | F02D 41/0055 |
| | | | | 123/568.16 |
| 2010/0300382 A1 * | 12/2010 | Yahagi | | C01B 3/323 |
| | | | | 123/3 |
| 2011/0010079 A1 * | 1/2011 | Shutty | | F02D 35/027 |
| | | | | 701/108 |
| 2011/0088674 A1 * | 4/2011 | Shutty | | F02D 41/0007 |
| | | | | 123/568.21 |
| 2011/0184632 A1 * | 7/2011 | Kang | | F02D 41/0007 |
| | | | | 701/109 |
| 2011/0191010 A1 * | 8/2011 | Russ | | 701/108 |
| 2012/0186564 A1 * | 7/2012 | Vigild | | F02D 41/1448 |
| | | | | 123/559.1 |

FOREIGN PATENT DOCUMENTS

JP          H10176577 A  *  6/1998
JP          2007162549 A  *  6/2007

* cited by examiner

METHODS AND SYSTEMS FOR A GAS CONSTITUENT SENSOR

TECHNICAL FIELD

The present application relates generally to a gas constituent sensor included in an intake system of an internal combustion engine.

BACKGROUND AND SUMMARY

Engine systems may utilize recirculation of exhaust gas from an engine exhaust system to an engine intake system (intake passage), a process referred to as exhaust gas recirculation (EGR), to reduce regulated emissions. An EGR system may include various sensors to measure the EGR. As one example, the EGR system may include an intake gas constituent sensor which may be employed to measure oxygen to determine the proportion of combusted gases in an intake passage of the engine. The output of such a sensor may vary as a function of pressure at the sensor location; for example, the output may vary as a function of the diffusion coefficient of the sensor. Due to manufacturing variability, for example, the diffusion coefficient may vary between sensors. As such, accuracy of the sensor output may be reduced.

The inventors herein have recognized the above issue and have devised an approach to at least partially address it. Thus, a method for a gas constituent sensor in an engine system which includes an EGR system is disclosed. The method includes, based on a gas constituent sensor output and a pressure sensor output, generating a correction while exhaust gas recirculation is off. The method further includes adjusting an amount of EGR based on the gas constituent sensor output and the correction while the exhaust gas recirculation is on.

The gas constituent sensor may be an intake gas constituent sensor, for example, which outputs an intake oxygen concentration. By generating the correction while the EGR is off, pressure variations in the intake system due to EGR may be reduced. Further, because the EGR is off, air flowing through the intake passage is substantially ambient air for which the oxygen concentration is known. As such, the correction for the gas constituent sensor may be obtained with a greater accuracy. Once the correction is applied to the sensor output, the amount of EGR is adjusted such that engine operation may be improved. For example, when the EGR is adjusted based on the corrected sensor output, the engine may operate with an air fuel ratio closer to a desired air fuel ratio.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to methods and systems for an engine system with an exhaust gas recirculation (EGR) system. In one example, a method comprises, based on a gas constituent sensor output and a pressure sensor output, generating a correction while EGR is off. The method further comprises adjusting an amount of EGR based on the gas constituent sensor output and the correction while the exhaust gas recirculation is on. In some embodiments, the gas constituent sensor may be an intake oxygen sensor. By generating the correction while the EGR is off, not only are pressure variations in the intake system reduced, but the oxygen concentration in the intake system is substantially the same as that of ambient air exterior to the engine system. In this way, the correction for the gas constituent sensor may be generated with a greater accuracy. Further, once the correction is obtained and applied to subsequent gas constituent sensor output, engine operation may be improved, as parameters such as EGR which affect the intake oxygen concentration may be adjusted accordingly.

Figure 1:
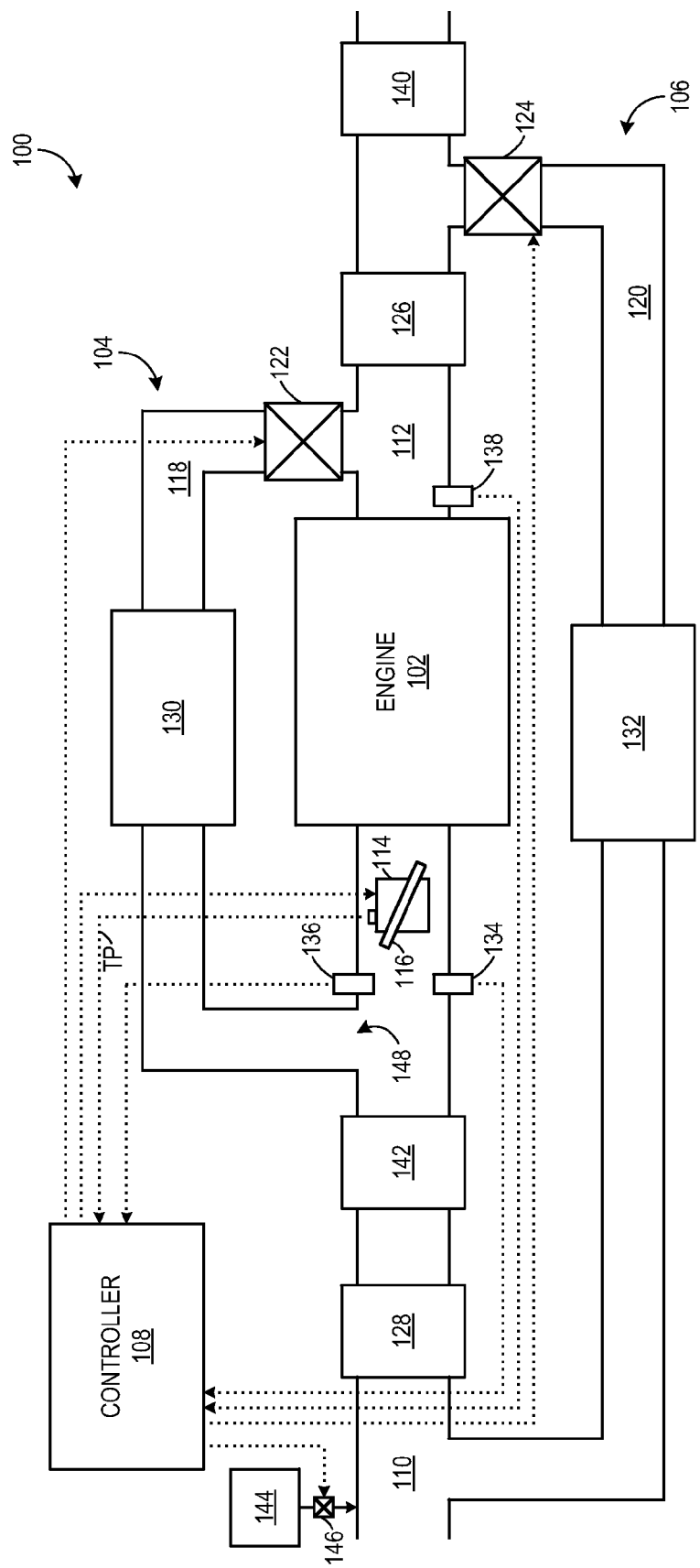
FIG. 1 shows a schematic diagram of an engine including an exhaust gas recirculation system and an intake gas constituent sensor.

Referring now to FIG. 1, is a schematic diagram of an engine system 100 with an engine 102, which may be included in a propulsion system of an automobile, is shown. As depicted, the engine system 100 includes an exhaust gas recirculation system including a high pressure EGR system 104 and a low pressure EGR system 106. The engine system 100 may be controlled at least partially by a control system including a controller 108.

The engine 102 may include a plurality of cylinders (not shown) configured to combust a mixture of charge air (e.g., intake air) and fuel, such as diesel, gasoline, alcohol (e.g., ethanol, methanol, etc.), a fuel blend, or another suitable fuel. The charge air may be delivered to the engine 102 via an intake passage 110, and the engine 102 may exhaust combustion gases via an exhaust passage 112.

The intake passage 110 may include one or more throttles, such as a throttle 114 having a throttle plate 116. In this particular example, a position of the throttle plate 116 may be varied by the controller 108 via signals provided to an electric motor or actuator included with the throttle 114, a configuration that is commonly referred to as electronic throttle control (ETC). In this manner, the throttle 114 may be operated to vary the intake air provided to the engine cylinders. The position of the throttle plate 116 may be provided to the controller 108 by throttle position signals TP. In the example depicted in FIG. 1, the intake passage 110 further includes a pressure sensor 134, such as a throttle inlet pressure (TIP) sensor configured to provide an indication of pressure upstream of the throttle 114. As will be described in greater detail below, the pressure sensor 134 may be further employed to determine a correction of an intake gas constituent sensor 136. The intake passage 110 may further include a mass air flow sensor (not shown) and a manifold air pressure sensor (not shown) for providing respective signals MAF and MAP to the controller 108.

In the disclosed embodiments, the EGR system routes a desired portion of exhaust gas from the exhaust passage 112 to the intake passage 110 via the high pressure EGR system 104 and/or the low pressure EGR system 106, depending on desired amounts of HP EGR and LP EGR. The high pressure EGR is routed from upstream of a turbine 126 of a turbocharger in the exhaust passage 112 to downstream of a compressor 128 of the turbocharger in the intake passage 110 via a high pressure EGR passage 118. The low pressure EGR is routed from downstream of the turbine 126 of the turbocharger to upstream of the compressor 128 of the turbocharger via a low pressure EGR passage 120. The amount of EGR provided to the intake passage 110 may be varied by the controller 108 via a high pressure EGR valve 122 coupled in the high pressure EGR system 104 and a low pressure EGR valve 124 coupled in the low pressure EGR system 106. In some embodiments, a throttle may be included in the exhaust to assist in driving the EGR, for example. Further, in the example embodiment shown in FIG. 1, the high pressure EGR system includes a high pressure EGR cooler 130 and the low pressure EGR system includes a low pressure EGR cooler 132 to reject heat from the recirculated exhaust gas to engine coolant, for example. In alternative embodiments, the engine 102 may include only a high pressure EGR system or only a low pressure EGR system.

The total amount of EGR and/or a high pressure EGR to low pressure EGR ratio may be controlled based on an exhaust gas constituent sensor 138 (e.g., an exhaust gas oxygen sensor) and/or the intake gas constituent sensor 136 (e.g., an intake oxygen sensor). The exhaust gas constituent sensor 138 is shown coupled to the exhaust passage 112 upstream of the turbine 126 and the intake gas constituent sensor 136 is shown coupled to the intake passage 110 downstream of a high pressure EGR inlet 148. The exhaust gas constituent sensors 136 and 138 may be any suitable sensors for providing an indication of exhaust or intake gas air/fuel ratio such as a linear oxygen sensor or UEGO (universal or wide-range exhaust gas oxygen), a two-state oxygen sensor or EGO, a HEGO (heated EGO), a $NO_X$, HC, or CO sensor. In the example embodiments described below with reference to FIGS. 2-4, the intake gas constituent sensor is an oxygen (e.g., $O_2$) sensor, for example. A correction for the intake gas constituent sensor 136 may be determined based on output from the pressure sensor 134 and output from the intake gas constituent sensor 136 over a range of boost pressure, for example, as will be described in greater detail below. Under some conditions, the EGR system may be used to regulate the temperature of the air and fuel mixture within the combustion chamber.

As stated above, the engine system 100 further includes a turbocharger with the turbine 126 arranged along the exhaust passage 112 and the compressor 128 arranged along the intake passage 110. For example, the compressor 128 may be at least partially driven by the turbine 126 (e.g., via a shaft). In this example, the amount of compression (e.g., boost) provided to one or more cylinders of the engine via the turbocharger may be varied by controller 108.

Further, in the example of FIG. 1, an emission control device 140 is shown arranged along the exhaust passage 112 downstream of the turbine 126 and the low pressure EGR passage 120. The emission control device 140 may be a selective catalytic reduction (SCR) system, three way catalyst (TWC), $NO_X$ trap, various other emission control devices, or combinations thereof. Further, in some embodiments, during operation of the engine 102, the emission control device 140 may be periodically reset by operating at least one cylinder of the engine within a particular air/fuel ratio, for example.

The engine system 100 further includes charge air cooler (CAC) 142. The CAC 142 is arranged along the intake passage 110 downstream of the compressor 128 for cooling the engine intake air after it has passed through the turbocharger and/or if it is diluted with low pressure EGR, for example.

Further, the engine system 100 includes a fuel vapor canister 144 which may be filled with adsorbent to temporarily trap fuel vapors (including vaporized hydrocarbons) during fuel tank refilling operations and "running loss" (that is, fuel vaporized during vehicle operation). In one example, the adsorbent used is activated charcoal. The controller 108 may be configured to adjust a fuel vapor purge valve 146 to control a flow of fuel vapors from the fuel vapor canister 144 to the intake passage 110, for example.

The controller 108 may be a microcomputer including the following, although not shown in FIG. 1: a microprocessor unit, input/output ports, an electronic storage medium for executable programs and calibration values (e.g., a read only memory chip), random access memory, keep alive memory, and a data bus. The storage medium read-only memory may be programmed with computer readable data representing non-transitory instructions executable by the microprocessor for performing the methods described below as well as other variants that are anticipated but not specifically listed. For example, the controller may receive communication (e.g., input data) from the various sensors, process the input data, and trigger the actuators in response to the processed input data based on instruction or code programmed therein corresponding to one or more routines. Example control routines are described herein with regard to FIGS. 2 and 4.

Figure 2:
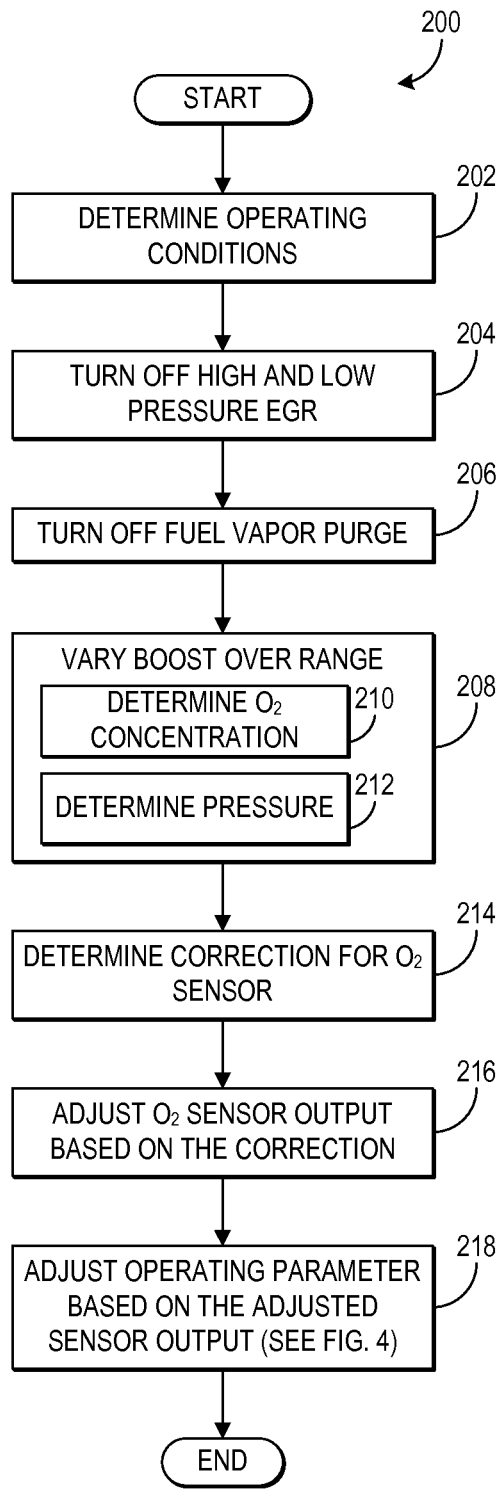
FIG. 2 shows a routine for estimating a correction of an intake gas constituent sensor.
Figure 4:
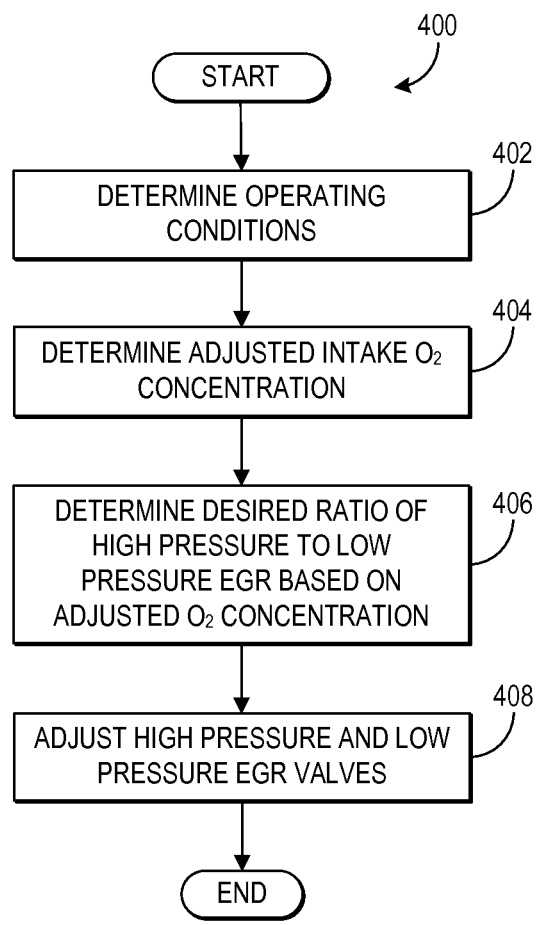
FIG. 4 shows a control routine for adjusting exhaust gas recirculation based on corrected intake gas constituent sensor output.

FIGS. 2 and 4 show flow charts illustrating routines for determining a correction for a gas constituent sensor and for adjusting an operating parameter based on corrected gas constituent sensor output, respectively. In the example embodiments described with reference to FIGS. 2 and 4, the gas constituent sensor is an oxygen sensor positioned in an intake passage and the adjusted operating parameter is EGR. It should be understood, however, the gas constituent sensor may detect any suitable intake gas constituent or exhaust gas constituent and any suitable operating parameter may be adjusted corresponding to the corrected gas constituent sensor output.

Referring now to FIG. 2, a routine 200 for determining a correction for an intake gas constituent sensor, such as the intake gas constituent sensor 136 described above with reference to FIG. 1, is shown. Specifically, the routine determines an oxygen concentration and pressure at a location in the intake passage downstream of an EGR inlet while the EGR is off. The oxygen concentration and pressure are determined over a range of turbocharger boost pressure such that a relationship, and thus a correction for the intake oxygen sensor, may be determined. In one example, the range may be at least a threshold range of boost pressures. In another example, the range may be at least from below atmospheric pressure to at least twice atmospheric pressure.

At 202, operating conditions are determined. As non-limiting examples, the operating conditions may include ambient temperature and pressure, boost, amount of EGR, air fuel ratio, etc.

Once the operating conditions are determined, the routine continues to 204 where high pressure and low pressure EGR are turned off. For example, the controller may send a signal to adjust the high pressure EGR valve and the low pressure EGR valve such that they are closed and exhaust gas does not flow from the exhaust passage to the intake passage.

Once the EGR is turned off, if fuel vapor purge is on, fuel vapor purge is turned off at 206. For example, the controller may send a signal to adjust the fuel vapor purge valve such that it is closed and fuel vapor does not flow from the fuel vapor canister to the intake passage. By turning off high pressure and low pressure EGR and fuel vapor purge, the air flowing through the intake passage may be substantially ambient air. As such, the oxygen concentration of the air may be known for example, and may be adjusted based on the ambient humidity.

At 208, the turbocharger is adjusted such that boost is varied over a range. For example, a turbocharger wastegate may be adjusted to vary the amount of boost. As an example, the range might be the whole boost range, for example, from zero boost pressure to a maximum level of boost pressure. In other examples, the boost may be varied over only part of the possible boost range. The span of the range may be adjusted depending on operating conditions, such as previous drive cycles and previous average maximum boost values. While the boost is varied, the intake oxygen concentration is determined at 210 (e.g., via the intake gas constituent sensor 136) at the various levels of boost and the intake pressure is determined at 212 (e.g., via the pressure sensor 134) at the various levels of boost.

Figure 3:
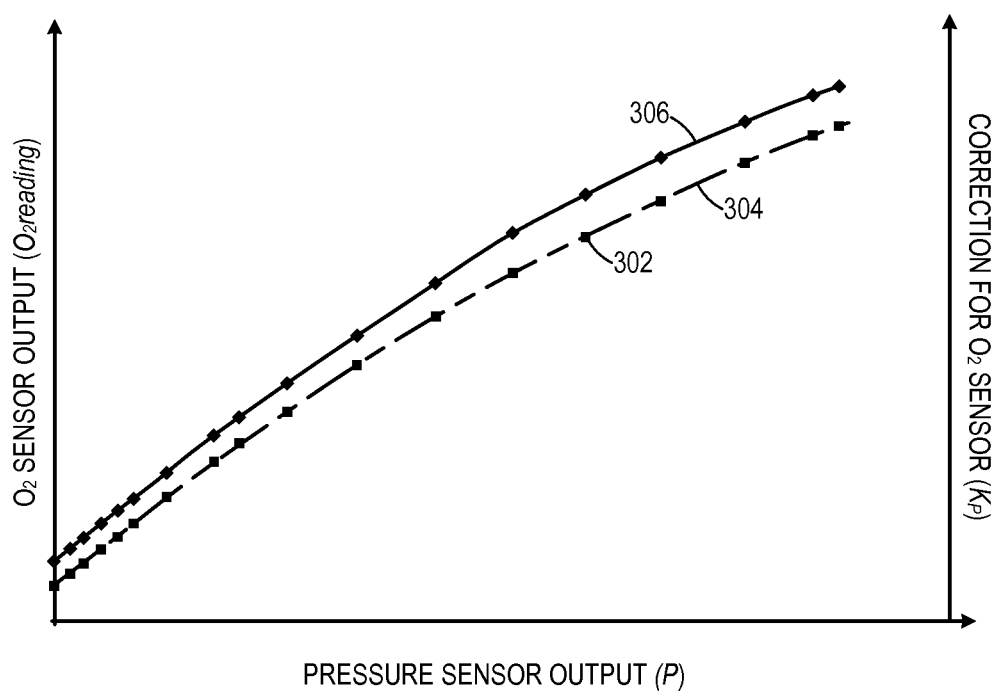
FIG. 3 shows a graph illustrating a correction of an intake gas constituent sensor.

At 214 a correction for the oxygen sensor is determined. The correction may be determined based on the intake oxygen concentration and the intake pressure determined at various levels of boost at 210 and 212. For example, FIG. 3 shows a graph illustrating a pressure correction equation determined based on intake oxygen concentration and intake pressure. The square points 302 shown in the graph in FIG. 3 indicate a calculated pressure correction factor, $K_p$. As an example, the pressure correction factor may be determined based on an equation such as:

$$K_p = \frac{O_2 reading}{baseO_2},$$

where $O_2$reading is the output of the sensor and base$O_2$ is a base $O_2$ concentration corrected for humidity. The square points 302 may be fitted to a curve 304, which has an equation such as:

$$K_p = aP^2 + bP + c,$$

where P is the intake pressure. Thus, the quadratic coefficients for a particular sensor may be adapted such that the correction may be determined based on the intake pressure, for example. Curve 306 shows measured oxygen sensor output versus intake pressure.

Continuing with FIG. 2, once the correction is determined, the oxygen sensor output is adjusted based on the correction. In other words, the pressure correction is applied to the oxygen sensor output such that the oxygen sensor output has a greater accuracy over a range of intake passage pressure, for example.

At 218, an operating parameter is adjusted based on the adjusted oxygen sensor output. As one example, the operating parameter may be EGR and the EGR may be adjusted according to the routine shown in FIG. 4, as described in greater detail below.

Thus, the correction for the intake oxygen sensor may be determined based on the intake pressure and intake oxygen concentration while the EGR is off. In this way, the intake oxygen sensor output may be corrected such that the output of the sensor has a higher accuracy over a range of system operating pressure.

Continuing to FIG. 4, a routine 400 for adjusting EGR responsive to a corrected indication of intake oxygen is shown. Specifically, the routine determines a desired ratio of an amount of high pressure EGR to an amount of low pressure EGR based on a corrected intake oxygen sensor output, such as the corrected intake oxygen sensor output determined in routine 200 of FIG. 2 described above.

At 402, operating conditions are determined. Non-limiting examples of the operating conditions include may include ambient temperature and pressure, boost, amounts of low pressure and high pressure EGR, air fuel ratio, intake oxygen concentration, etc.

Once the operating conditions are determined, the adjusted intake oxygen concentration is determined at 404. For example, the adjusted intake oxygen concentration may be the corrected oxygen concentration determined at 216 of routine 200.

Once the adjusted oxygen concentration is determined, the desired ratio of high pressure EGR to low pressure EGR is determined based on the adjusted oxygen concentration at 406. For example, the intake oxygen sensor may be used to determine the proportion of combusted gases in an intake passage of the engine based on the intake oxygen concentration. When the intake oxygen sensor output is adjusted based on the correction, the calculated proportion of combusted gases in the intake passage may change. As such, the amount of EGR and the ratio of high pressure EGR to low pressure EGR may be adjusted. As one particular example, when the corrected intake oxygen concentration increases such that the intake oxygen concentration is higher than desired, the amount of EGR may be reduced. On the other hand, when the corrected intake oxygen concentration decreases such that the intake oxygen concentration is less than desired, the amount of EGR may be increased.

In some examples, the high pressure EGR may be increased and the low pressure EGR may be reduced. In other examples, the high pressure EGR may be reduced and the low pressure EGR may be increased. In still other examples, both the high pressure low pressure EGR may be increased. In other examples, both the high pressure and low pressure EGR may be reduced. In yet other examples, only the high pressure EGR or the low pressure EGR may be increased or reduced.

After the desired ratio of high pressure EGR to low pressure EGR is determined, the routine proceeds to 408 where the high pressure and low pressure EGR valves are adjusted such that the amount of high pressure EGR and low pressure EGR meet the desired amount of high pressure EGR and low pressure EGR determined at 406.

Thus, responsive to a corrected intake oxygen sensor output, one or both of the high pressure and low pressure EGR may be adjusted. In this manner, engine operation may be improved, as the amount of EGR is adjusted based on an intake oxygen concentration that is determined with increased accuracy.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system. It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method for controlling an internal combustion engine, the engine comprising a controller with an electronic storage medium programmed with computer readable data representing non-transitory instructions executable by the controller for performing the method, the method comprising:
    closing an exhaust gas recirculation valve;
    adjusting a turbocharger wastegate valve to vary a boost pressure amount from zero boost pressure to a maximum boost level pressure while detecting the boost pressure with a pressure sensor and detecting a gas constituent sensor output;
    at each of a plurality of detected boost pressures, generating a pressure correction factor based on the detected gas constituent sensor output;
    fitting the generated pressure correction factors to a curve and determining a quadratic pressure correction equation of the curve;
    correcting a subsequent gas constituent sensor output via the equation; and
    opening the exhaust gas recirculation valve, an opening amount of the exhaust gas recirculation valve adjusted based on the corrected gas constituent sensor output.

2. The method of claim 1, wherein the gas constituent sensor and the pressure sensor are positioned downstream of an exhaust gas recirculation inlet in an intake passage of the engine.

3. The method of claim 2, wherein the exhaust gas recirculation inlet is a high pressure exhaust gas recirculation inlet disposed downstream of a compressor of the turbocharger.

4. The method of claim 1, wherein adjusting the amount of exhaust gas recirculation includes adjusting amounts of high pressure exhaust gas recirculation and low pressure exhaust gas recirculation.

5. The method of claim 4, wherein adjusting the amounts of high pressure exhaust gas recirculation and low pressure exhaust gas recirculation includes increasing the amount of high pressure exhaust gas recirculation and reducing the amount of low pressure exhaust gas recirculation.

6. The method of claim 1, further comprising generating the pressure correction factors while a fuel vapor canister purge valve is closed and fuel vapor canister purge is not flowing.

7. The method of claim 1, wherein the gas constituent sensor is an oxygen sensor.

8. A method for controlling an internal combustion engine, the engine comprising a controller with an electronic storage medium programmed with computer readable data representing non-transitory instructions executable by the controller for performing the method, the method comprising:
    closing an exhaust gas recirculation valve;
    adjusting a turbocharger wastegate valve to vary a boost pressure amount from zero boost pressure to a maximum level of boost pressure while detecting a plurality of boost pressures with a boost pressure sensor and detecting a plurality of intake gas constituent sensor outputs;
    determining a quadratic pressure correction equation based on the detected plurality of boost pressures and the detected plurality of intake gas constituent sensor outputs;
    correcting a subsequent output of the intake gas constituent sensor via the equation; and
    opening the exhaust gas recirculation valve, an opening amount of the exhaust gas recirculation valve adjusted based on the corrected intake gas constituent sensor output.

9. The method of claim 8, wherein the intake gas constituent sensor and the pressure sensor are disposed downstream of a high pressure exhaust gas recirculation inlet in an intake passage of the engine.

10. The method of claim 8, wherein adjusting the opening amount of the exhaust gas recirculation valve includes adjusting an opening amount of a high pressure exhaust gas recirculation valve and an opening amount of low pressure exhaust gas recirculation valve.

11. The method of claim 10, wherein adjusting the opening amount of the high pressure exhaust gas recirculation valve and the low pressure exhaust gas recirculation valve includes adjusting a ratio of high pressure exhaust gas recirculation to low pressure exhaust gas recirculation.

12. The method of claim 8, wherein the intake gas constituent sensor is an oxygen sensor.

13. A system, comprising:
    an engine with an intake passage and an exhaust passage;
    a turbocharger including a compressor coupled in the intake passage for generating a boost pressure;
    a turbocharger wastegate valve;
    a high pressure exhaust gas recirculation system and a low pressure exhaust gas recirculation system, the high pressure exhaust gas recirculation system having a high pressure exhaust gas recirculation inlet disposed downstream of the compressor;
    a gas constituent sensor positioned downstream of the high pressure exhaust gas recirculation inlet and configured to output a gas constituent concentration;
    a pressure sensor positioned downstream of the high pressure exhaust gas recirculation inlet and configured to output an intake pressure; and
    a control system in communication with the sensors, the control system including non-transitory instructions executable by a controller to adjust a high pressure exhaust gas recirculation valve to turn off high pressure exhaust gas recirculation, adjust a low pressure exhaust gas recirculation valve to turn off low pressure exhaust gas recirculation, generate a quadratic pressure correction equation based on outputs from the gas constituent sensor and the pressure sensor over a whole boost range from zero boost pressure to a maximum level of the boost pressure, correct a subsequent output of the gas constituent sensor via the equation, and adjust the high pressure exhaust gas recirculation valve and low pressure exhaust gas recirculation valve to adjust amounts of high pressure and low pressure exhaust gas recirculation based on corrected gas constituent sensor output.

14. The system of claim 13, wherein the gas constituent sensor is an oxygen sensor configured to output an oxygen concentration.

15. The system of claim 13, wherein adjusting the amounts of high pressure and low pressure exhaust gas recirculation includes adjusting a ratio of high pressure exhaust gas recirculation to low pressure exhaust gas recirculation.

16. The system of claim 13, wherein the control system is further configured to adjust the wastegate valve to vary the boost pressure of the turbocharger while the equation is generated.

17. The system of claim 13, further comprising a fuel vapor canister, and wherein the control system is further configured to turn off purging of the fuel vapor canister by sending a signal with the controller to close a fuel vapor canister purge valve while the equation is generated.

* * * * *